(12) United States Patent
Kawamura

(10) Patent No.: US 6,643,021 B1
(45) Date of Patent: Nov. 4, 2003

(54) METHOD FOR CONTROLLING OPTICAL PROPERTY MEASUREMENT SYSTEM

(75) Inventor: Tatsurou Kawamura, Kyotanabe (JP)

(73) Assignee: Matsushita Electric Industrial Co., Ltd., Osaka-fu (JP)

( * ) Notice: Subject to any disclaimer, the term of this patent is extended or adjusted under 35 U.S.C. 154(b) by 0 days.

(21) Appl. No.: 09/487,852

(22) Filed: Jan. 19, 2000

(30) Foreign Application Priority Data

Jan. 22, 1999 (JP) .......................................... 11-014930

(51) Int. Cl.⁷ ............................................... G01N 21/00
(52) U.S. Cl. ..................................................... 356/436
(58) Field of Search .................................. 356/436–440

(56) References Cited

U.S. PATENT DOCUMENTS

| | | | |
|---|---|---|---|
| 4,320,977 A | * | 3/1982 | Matsumoto ................. 356/440 |
| 5,247,558 A | | 9/1993 | Hendrix et al. |

FOREIGN PATENT DOCUMENTS

| | | |
|---|---|---|
| CH | 636 200 A5 | 5/1983 |
| JP | 56-135160 U | 3/1980 |
| JP | 56-154646 A | 11/1981 |
| JP | 60-161546 A | 8/1985 |
| JP | 61-183608 U | 11/1986 |
| JP | 01-59852 U | 4/1989 |
| JP | 03-91958 U | 9/1991 |
| JP | 06-007054 | 1/1994 |
| JP | 09-054076 | 2/1997 |
| JP | 10-322010 | 12/1998 |
| WO | WO 98/00701 | 1/1998 |

\* cited by examiner

*Primary Examiner*—Frank G. Font
*Assistant Examiner*—Amanda Merlino
(74) *Attorney, Agent, or Firm*—Akin, Gump, Strauss, Hauer & Feld, L.L.P.

(57) ABSTRACT

The present invention provides a controlling method of optical property measurement system wherein optical properties of a liquid sample are measured by projecting first light to analyze transmitted light, the method comprising the steps of projecting additional light to a path of the first light or in a periphery thereof to detect the presence or absence of bubbles and/or particles which may interfere with transmission of the first light, based on an intensity of transmitted light of the second light, and removing the bubbles and/or particles when their presence is confirmed. This eliminates the need of detaching the sample cell from an optical system to introduce or excrete the sample and facilitates precise measurement of optical properties of sample even when interfering substances are present in the sample cell.

12 Claims, 3 Drawing Sheets

F I G. 1
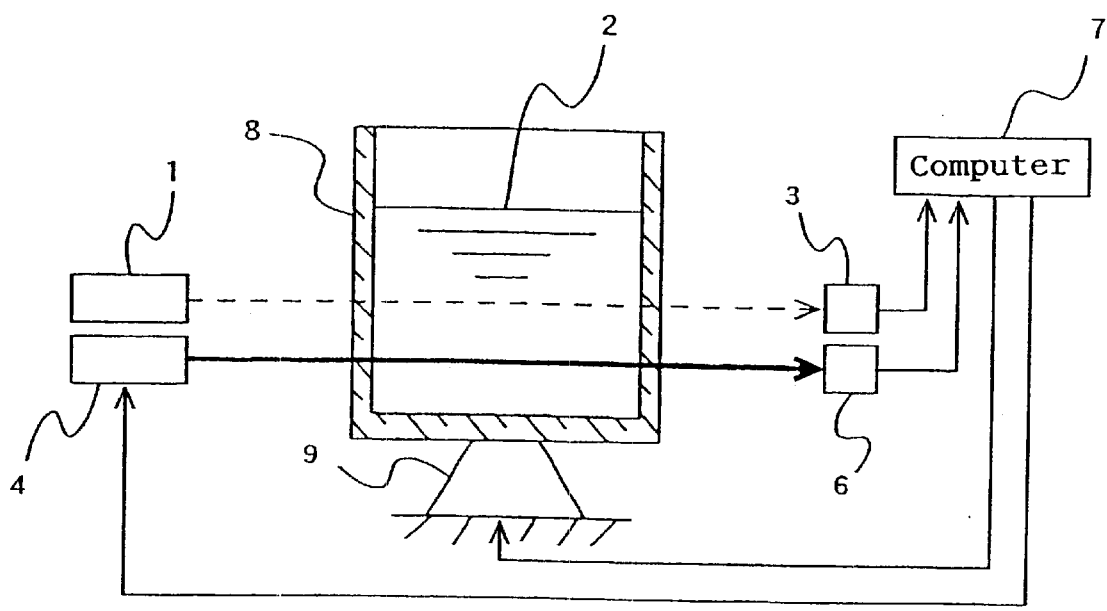

METHOD FOR CONTROLLING OPTICAL PROPERTY MEASUREMENT SYSTEM

BACKGROUND OF THE INVENTION

The present invention relates to measurement of optical properties of a liquid sample, more particularly to a method for controlling an optical property measurement system.

When a sample is to be measured for the optical properties, then it should be placed in a sample cell so that light is transmitted therethrough. The sample cell is generally made of a glass or the like having a rectangular shape and has a structure where light is transmitted between a pair of transparent transmission planes.

In general, the sample cell has an opening at its upper part through which a preformulated sample is introduced into or excreted from the sample cell using a dropper, pipette, or syringe.

Exchange of sample is routinely performed for each sample cell. At that time, if bubbles or remaining undissolved particles of a solute are present on an optical path of light for measurement, they interfere with precise measurement, resulting in impaired measurement accuracy. Particularly, if the sample is introduced into such a sample cell that is fixed to an optical system or when a solute powder is dissolved in a solvent inside the sample cell to formulate a sample solution, there arise problems that bubbles are likely to generate during handling or the solute powder is likely to remain undissolved in the solvent. This makes it difficult to introduce the sample into or excrete it from the sample cell or to formulate a sample to be analyzed inside the sample cell, while the sample cell is installed inside the optical system.

Therefore, in order to prevent such problems, the sample cell is conventionally detached from the optical system to place the sample inside the sample cell and then install the sample containing sample cell in the optical system. Even if the sample solution is formulated inside the sample cell to measure the optical properties of the sample, the sample cell is installed in the optical system after formulation of sample solution.

As such, sample exchange and internal washing of the sample cell requires detachment of the sample cell from the optical system, rendering the operation much laborious and time-consuming. Furthermore, despite potential interference with the measurement of fine interfering substances, which are invisible with naked eyes, it is impossible to visually confirm all the interfering substances such as bubbles on the optical path without fail.

Moreover, when bubbles or particles are floating in the sample, for example, it is difficult to make exact estimation of a position of optical path when the sample cell is installed inside the optical system. The presence of undissolved solute represents that the liquid as the sample is not in an intended condition. As such, the presence of miscellaneous interfering substances renders it difficult to make precise measurement.

An object of the present invention is to solve the above-mentioned problems and provide a controlling method of optical property measurement system which does not require detachment of the sample cell from the optical system for introduction and excretion of sample solution and facilitates accurate measurement of optical properties of the sample even in the presence of interfering substances such as bubbles inside the sample cell.

BRIEF SUMMARY OF THE INVENTION

The present invention provides a method for controlling optical property measurement system wherein optical properties of a liquid sample are measured by projecting first light to said liquid sample accommodated in a sample cell to analyze transmitted light therethrough, said method comprising the steps of:

projecting second light to a path of said first light projected to said liquid sample or in a periphery of said path of said first light to detect the presence or absence of bubbles and/or particles in said sample which may interfere with transmission of said first light projected to said sample, based on an intensity of transmitted light of said additional second light, and vibrating said sample cell upon detection of the presence of bubbles and/or particles in said sample to remove said bubbles and/or particles from said path of said second light transmitted to said sample.

Further, the present invention provides a method for controlling optical property measurement system wherein optical properties of a liquid sample are measured by projecting first light to said liquid sample accommodated in a sample cell to analyze transmitted light therethrough, said method comprising the steps of:

projecting additional second light to a path of said first light projected to said liquid sample or in a periphery of said path of said light to detect the presence or absence of bubbles and/or particles in said sample which may interfere with transmission of said first light projected to said sample, based on an intensity of transmitted light of said additional second light, and stirring said sample upon detection of the presence of bubbles and/or particles in said sample to remove said bubbles or particles from said path of said first light transmitted to said sample.

Further, the present invention provides a method for controlling optical property measurement system wherein optical properties of a liquid sample are measured by projecting first light to said liquid sample accommodated in a sample cell to analyze transmitted light therethrough, said method comprising the steps of:

projecting additional second light to a path of said first light projected to said liquid sample or in a periphery of said path of said first light to detect the presence or absence of bubbles and/or particles in said sample which may interfere with transmission of said first light projected to said sample, based on an intensity of transmitted light of said additional second light, and sliding a member along an inner wall of an entrance plane and an exit plane of said first light in said sample cell upon detection of the presence of bubbles and/or particles in said sample to remove said bubbles and/or particles attached to said inner wall.

Further, the present invention provides a method for controlling optical property measurement system wherein optical properties of a liquid sample are measured by projecting first light to said liquid sample accommodated in a sample cell to analyze transmitted light therethrough, comprising the steps of:

projecting additional second light to a path of said first light projected to said liquid sample or in a periphery of said path of said light to detect the presence or absence of bubbles and/or particles in said sample which may interfere with transmission of said first light projected to said sample, based on an intensity of transmitted light of said additional second light, and inclining said sample cell upon detection of the presence of bubbles and/or particles in said sample.

In this case, said sample cell may have a cylindrical shape such that said first light comes in one end face and comes out other end face.

Also, when inclining the sample cell, tilt of an axis of the sample cell may be altered. Of course, the position of the axis is varied depending on the form of the sample cell.

The above-mentioned method for controlling optical property measurement system wherein said sample is formulated inside said sample cell preferably further comprises a step of destroying bubbles and/or particles of a solute upon detection of bubbles and/or remaining undissolved particles of the solute during formulation of said sample in said step of detecting bubbles and/or particles by subsequently applying a vibration to said sample cell, stirring said sample, or inclining said sample cell, and confirming disappearance of said bubbles and/or particles of the solute prior to actual measurement.

Also, it is oreferable that said first light for measuring optical properties and second light for detecting the presence or absence of bubbles and/or particles in said sample which may interfere with transmission of said first light are projected to said sample while overlapping the two.

Further, it is preferable that said first light for measuring optical properties is employed for said second light for detecting the presence or absence of bubbles and/or particles in said sample which may interfere with transmission of the first light.

While the novel features of the invention are set forth particularly in the appended claims, the invention, both as to organization and content, will be better understood and appreciated, along with other objects and features thereof, from the following detailed description taken in conjunction with the drawings.

BRIEF DESCRIPTION OF THE SEVERAL VIEWS OF THE DRAWING

FIG. 1 is a schematic view illustrating a structure of a spectropolarimeter used in one example in accordance with the present invention.

DETAILED DESCRIPTION OF THE INVENTION

Figure 2:
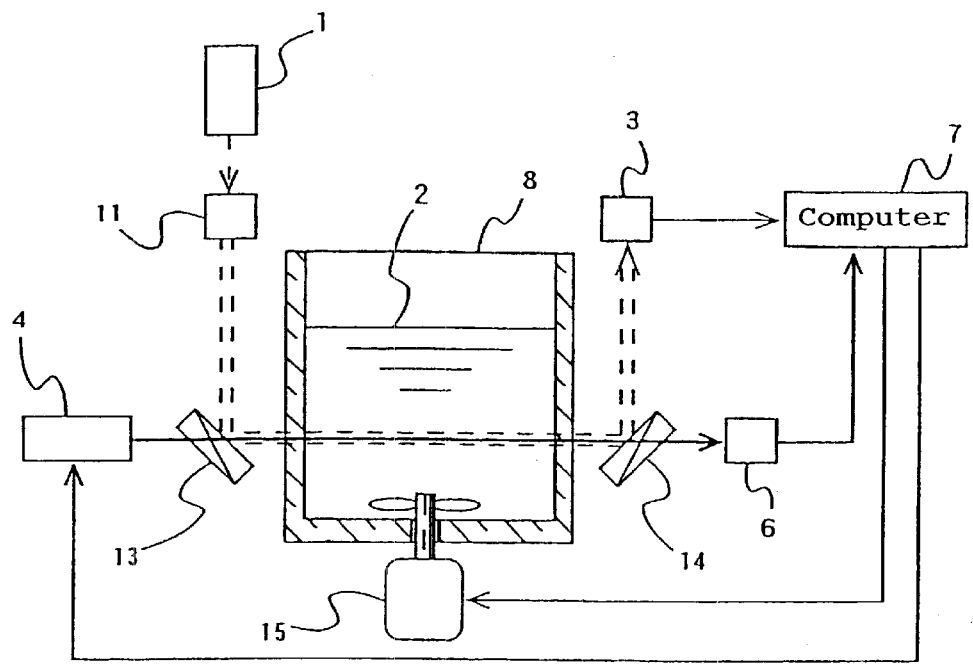
FIG. 2 is a schematic view illustrating a structure of a spectropolarimeter used in another example in accordance with the present invention.

As mentioned before, the method for controlling optical property measurement system in accordance with the present invention projects additional second light to the path of the first light for measurement in the liquid sample accommodated in the sample cell or in a periphery of the path of the first light to detect the presence or absence of bubbles and/or particles in the sample, which may interfere with transmission of the first light for measurement, based on an intensity of transmitted light of the additional second light through the sample. Upon detection of bubbles and/or particles in the sample, the method applies a vibration to the sample cell, stirs the sample or sliding a removing member whereby those interfering substances can be cleared from the path of the first light in the sample.

The method for controlling optical property measurement system in accordance with the present invention wherein optical properties of a liquid sample are measured by projecting first light to the liquid sample accommodated in a sample cell to analyze transmitted first light therethrough comprises the steps of projecting additional second light to a path of the first light projected to the liquid sample or in a periphery of the path of the first light to detect the presence or absence of bubbles and/or particles in the sample, which may interfere with transmission of the first light projected to the sample, based on an intensity of transmitted light of the additional second light, and vibrating the sample cell upon detection of the presence of bubbles and/or particles in the sample to clear the bubbles and/or particles from the path of the first light in the sample.

Another method for controlling optical property measurement system in accordance with the present invention wherein optical properties of a liquid sample are measured by projecting first light to the liquid sample accommodated in a sample cell to analyze transmitted first light therethrough comprises the steps of projecting additional second light to a path of the first light projected to the liquid sample or in a periphery of the path of the first light to detect the presence or absence of bubbles and/or particles in the sample which may interfere with transmission of the first light projected to the sample, based on an intensity of transmitted light of the additional second light, and stirring the sample upon detection of the presence of bubbles and/or particles in the sample to clear the bubbles and/or particles from the path of the first light in the sample.

Still another method for controlling optical property measurement system in accordance with the present invention wherein optical properties of a liquid sample are measured by projecting first light to the liquid sample accommodated in a sample cell to analyze transmitted first light therethrough comprises the steps of projecting additional second light to a path of the first light projected to the liquid sample or in a periphery of the path of the firs light to detect the presence or absence of bubbles and/or particles in the sample which may interfere with transmission of the first light projected to the sample, based on an intensity of transmitted light of the additional second light, and sliding a removing member along an inner wall of an entrance plane and an exit plane of the light in the sample cell upon detection of the presence of bubbles and/or particles in the sample to remove the bubbles and/or particles attached to the inner wall.

Bubbles and particles in liquids are liable to adhere to the wall surface. Adhesion of those substances in the sample to a transmission plane of the sample cell greatly interferes with measurement of optical properties of the sample. Further, there is a case that the bubbles and particles adhered to the wall surface are relatively difficult to be removed by the above-mentioned stirring or vibration. Therefore, those substances are directly cleared off dynamically using the removing member. Dynamic removal ensures removal of any interfering substance facilitating highly reliable measurement.

A still further method for controlling optical property measurement system in accordance with the present invention wherein optical properties of a liquid sample are measured by projecting first light to the liquid sample accommodated in a sample cell to analyze transmitted light therethrough, comprising the steps of projecting additional light to a path of the first light projected to the liquid sample or in a periphery of the path of the first light to detect the presence or absence of bubbles and/or particles in the sample which may interfere with transmission of the first light projected to the sample, based on an intensity of transmitted light of the additional second light, and inclining the sample cell upon detection of the presence of bubbles and/or particles in the same.

The sample cell may have a cylindrical shape such that the first light comes in one end face and goes out the other face. When inclining the sample cell, it may be preferable to alter tilt of an axis of the sample cell with respect to the direction of gravity. The axis may be varied depending upon the form of the sample cell. In case of the cylindrical shape, the axis is preferably a longitudinal one in view of optical path length per a unit voulume of the sample cell.

According to any of the above-mentioned methods, interfering substances such as bubbles and/or particles in the sample accommodated in the sample cell can be detected efficiently and cleared or destroyed from the sample by applying a vibration, stirring, etc. This enables a series of operations including introduction, exchange and formulation of sample in the sample cell while retaining the sample cell in the optical system and the subsequent precise measurement which have been difficult due to easy formation of bubbles and undissolved particles.

Moreover, since the method can detect the presence of undissolved solute to promote dissolution of the undissolved solute, optical properties of the sample can be measured precisely under stable conditions.

As a result, handling of such sample as urine which is likely to produce bubbles in measuring the optical properties and reliability of measurement can be improved drastically which results in promotion of automated measurement. A particularly effective measure for accelerating dissolution of undissolved solute particles on the optical path is to stir the sample.

As such, according to any of the method for controlling optical property measurement system in, accordance with the present invention, impairment of measurement accuracy due to bubbles and/or undissolved solute can be prevented thereby facilitating measurement of higher reliability. Moreover, the method allows formulation of sample in the sample cell, enabling efficient and labor saving testing.

The above-mentioned series of operations are effective during optical measurement, not to mention before optical measurement. If the presence of interfering substances such as bubbles and/or particles in the sample is detected during measurement while continuing monitoring of their presence, then those interfering substances may be removed or destroyed from the optical path be means of vibration by discontinuing the measurement.

At that time, the use of more intense light as the additional second light results in a greater change in optical quantity due to the interfering substances. Therefore, if the additional second light for detecting the interfering substances has a greater intensity than the first light for measuring the optical properties, fine bubbles and particles which are not detectable by the additional second light substantially have no effect on the actual optical measurement. As such, the use of a greater intensity for the additional second light than that for the first light enables more precise measurement.

If the sample is to be formulated inside the sample cell, it is formulated while detecting the presence of bubbles and/or remaining undissolved solute particles and if detected, they are destroyed by subsequently applying a vibration to the sample cell, stirring the sample or altering tilt of the axis of the sample cell. Optical measurement starts after confirmation of their disappearance.

Projecting, to the sample, the above-mentioned first light for measuring the optical properties and the additional second light for detecting bubbles and/or particles in the sample which may interfere with transmission of the first light after overlapping the both lights enables real time detection of the presence of those substances.

Particularly, continued monitoring during measurement enables highly reliable measurement.

Furthermore, if the additional second light for detection is given a greater diameter than that of the first light for measurement to let the additional light cover the first light entirely, it is possible to ensure detection of any interference of the bubbles and particles with the additional light for measurement.

As mentioned previously, the first light for measuring the optical properties may be employed for the additional second light for detecting bubbles and/or particles in the sample which may interfere with transmission of the first light. The first light and the second light may be transmitted from an identical light source. Further, the the first light and the additional second light may have same optical properties.

In the following, the present invention will be described more specifically referring to preferred examples and figures.

EXAMPLE 1

In this example, spectrophotometry will be described.

FIG. 1 shows a schematic view of a spectrophotometer.

A semiconductor laser module 1 projects almost parallel light of a specific wavelength toward a sample cell 8 as shown by a dashed line in the figure. The sample cell 8 accommodates a liquid sample 2. A plane of entrance of light (hereinafter referred to as "entrance plane") into the sample cell 8 and an opposite surface, that is, a plane of exit of light (hereinafter referred to as "exit plane") are both transparent. An optical sensor 3 senses and detects light which was projected from the semiconductor laser module 1 and has transmitted through the sample 2.

A wavelength variable light source (tunable laser) 4 having a lamp and a spectroscopic element projects almost parallel light toward the entrance plane of the sample cell 8 as shown by a continuous line in the figure. Another optical sensor 6 senses and detects light which was projected from the wavelength variable light source 4 and has transmitted through the sample 2.

If protein is the light absorbing component of the sample, a range of absorption wavelength of the sample is between 190 and 300 nm. The wavelength variable light source 4 emits almost parallel light having a wavelength in a range of 190 to 700 nm, which range includes the above-mentioned range, an intensity in a range of 100 to 400 $\mu$W and a beam diameter of 3.0 mm.

The semiconductor laser module 1 projects almost parallel light having a wavelength of 780 nm which is outside a range of absorbance wavelength toward the sample 2.

A computer 7 controls the wavelength variable light source 4 and sweeps a wavelength of light emitted from the light source 4. The computer 7 also monitors, records and analyzes an output signal of the optical sensor 3.

The sample cell 8 is placed on a vibration table 9. The vibration table 9 vibrates the sample cell 8 based on a command signal from the computer 7.

In the following, an operation of the spectropolarimeter will be described.

First, a liquid sample is introduced into the sample cell 8 or formulated by introducing a solvent and a solute into the sample cell 8. If bubbles generating during sample formulation or remaining undissolved solute particles are present on the optical path of projected light from the semiconductor laser module 1, the light quantity which can arrive at the optical sensor 3 decreases greatly. The presence of such interfering substances on the optical path results in a greater decrease of output signal from the optical sensor 3 than that obtained in the absence of any interfering substances on the optical path. The computer 7 detects the presence of those interfering substances based on a magnitude or a change of output signal from the optical sensor 3.

Upon detection of the presence of those interfering substances, the computer 7 controls the vibration table 9 to vibrate the sample cell 8. As a result, the sample in the sample cell 8 is stirred and the interfering substances are shifted from the optical path. The vibration also promotes disappearance of bubbles and dissolution of not yet dissolved solute particles. The computer 7 does not make absorption measurement during detecting the interfering substances. When the interfering substances are eliminated or shifted to disappear from the optical path, the output signal from the optical sensor 3 recovers and is stabilized. When the solute particles remain undissolved, complete dissolution of the remaining solute to make a uniform concentration of the sample 2 can be confirmed by recovery and stabilization of the output signal from the optical sensor 3.

When the output signal from the optical sensor 3 is stabilized, the computer 7 controls the vibration table 9 to stop application of a vibration and starts absorption measurement. Namely, the computer 7 controls the wavelength variable light source 4 to project light and analyzes an output signal from the optical sensor 6 while sweeping a wavelength of the light.

As such, confirmation of complete dissolution of the solute prior to the measurement enables measurement of optical properties of a sample at a coincident concentration to an actual amount of the original.

When the liquid sample is formulated in the sample cell 8, the presence of undissolved solute particles and bubbles generating during their dissolution is detected based on the output signal from the optical sensor 3.

As discussed above, detection of interference with the measurement by the interfering substances such as bubbles and solute particles and the subsequent vibration of the sample cell result in successful removal or disappearance of those substances from the optical path. As a result, impairment of measurement accuracy due to those substances can be prevented.

It is also possible to remove or destroy the bubbles and particles as interfering substances from the optical path during measurement by vibrating the sample cell 8 upon detection of the presence of bubbles and particles while monitoring them.

EXAMPLE 2

In this example, too, measurement using a spectrophotometer will be described. FIG. 2 is a schematic view of the spectrophotometer used in this example. Unless otherwise stated, the same reference numerals as in Example 1 will be used in the following examples.

As in Example 1, the semiconductor laser module 1 projects almost parallel light of a specific wavelength toward the sample cell 8 as shown by a dashed line in the figure. The sample cell 8 accommodates the liquid sample 2.

The wavelength variable light source 4 projects almost parallel light toward the entrance plane of the sample cell 8 as shown by a continuous line in the figure.

As in Example 1, if the light absorbing component of the sample is protein, the wavelength variable light source 4 emits almost parallel light having a wavelength in a range of 190 to 700 nm, which range includes the above-mentioned absorption wavelength range of protein, an intensity in a range of 100 to 400 $\mu W$ and a beam diameter of 3.0 mm.

The semiconductor laser module 1 projects almost parallel light having a beam diameter of 2.0 mm and a wavelength of 780 nm which is outside the range of absorbance wavelength (toward the sample 2).

A beam expander 11 composed of lens, etc. converts the almost parallel light projected from the semiconductor laser module 1 into light having a larger beam diameter of 4.0 mm.

Dichroic mirrors 13 and 14 reflect light having a wavelength of about 730 nm or more and transmit other light. The light which was projected from the semiconductor laser module 1 and has bypassed the beam expander 11 is reflected by the dichroic mirror 13.

On the other hand, the light which was projected from the wavelength variable light source 4 transmits through the dichroic mirror 13 and advances to the sample cell 8. The light coming from the semiconductor laser module 1 and then reflected by the dichroic mirror 13 and the light coming from the wavelength variable light source 4 and then transmitting through the dichroic mirror 13 are overlapped, and the overlapped light advances to the sample cell 8. The light projected by the semiconductor laser module 1 is greater in beam diameter than that projected by the wavelength variable light source 4 and therefore encloses the latter light. The light which has passed through the sample cell 8 is separated by the dichroic mirror 14. The optical sensor 3 detects the light reflected by the dichroic mirror 14, that is, the light which was projected from the semiconductor laser module 1 and has bypassed the sample cell 8. The optical sensor 6 detects the light transmitting through the dichroic mirror 14, that is, the light which was projected from the wavelength variable light source 4 and has bypassed the sample cell 8.

The computer 7 sweeps a wavelength of light projected by the wavelength variable light source 4, and records and analyzes the output signal from the optical sensor 6. The computer 7 also monitors the output signal from the optical sensor 3. The sample cell 8 has a stirrer 15 formed at the end face which operates based on the command signal from the computer 7.

The computer 7 detects the presence of interfering substances such as bubbles and undissolved solute particles in the sample 2 based on the output signal from the optical sensor 3, that is, light quantity projected by the semiconductor laser module 1 and arriving at the optical sensor 3. Upon detection of the presence of such interfering substances, the computer 7 activates the stirrer 15 to stir the sample 2 in the sample cell 8.

The computer 7 does not make any absorption measurement during its detection of interfering substances. When the interfering substances are removed or shifted to disappear from the optical path, the output signal from the optical sensor 3 recovers and is stabilized. Upon stabilization of the output signal from the optical sensor 3, the computer 7 stops stirring and starts measurement.

EXAMPLE 3

Figure 3:
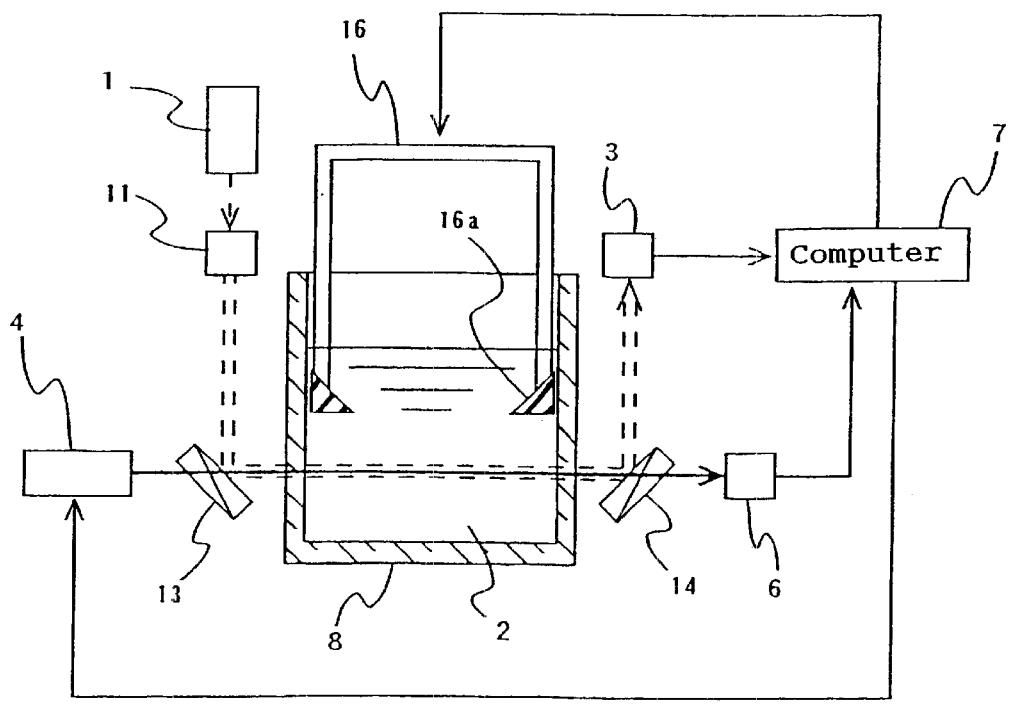
FIG. 3 is a schematic view illustrating a structure of a spectropolarimeter used in still another example in accordance with the present invention.

In this example, too, measurement using a spectrophotometer will be described. FIG. 3 shows a schematic view of the spectrophotometer used in this example.

As in Example 2, the spectrophotometer of the present example overlaps the light for detection and the light for optical measurement and projects the overlapped light to the sample to be analyzed.

Upon detection of the presence of interfering substances such as bubbles and undissolved solute particles in the sample 2, the bubbles and particles adhered to the wall surface of the sample cell 8 are removed by moving a removing member 16 up and down along an inner wall of a transparent side of the sample cell 8. As shown in FIG. 3, the removing member 16 has a columnar silicone rubber wiper 16a, for example. When the removing member 16 is moved up and down, the wiper 16a slides along the inner wall of the transparent side of the sample cell 8 to remove the adhering interfering substances to the wall surface.

EXAMPLE 4

Figure 4:
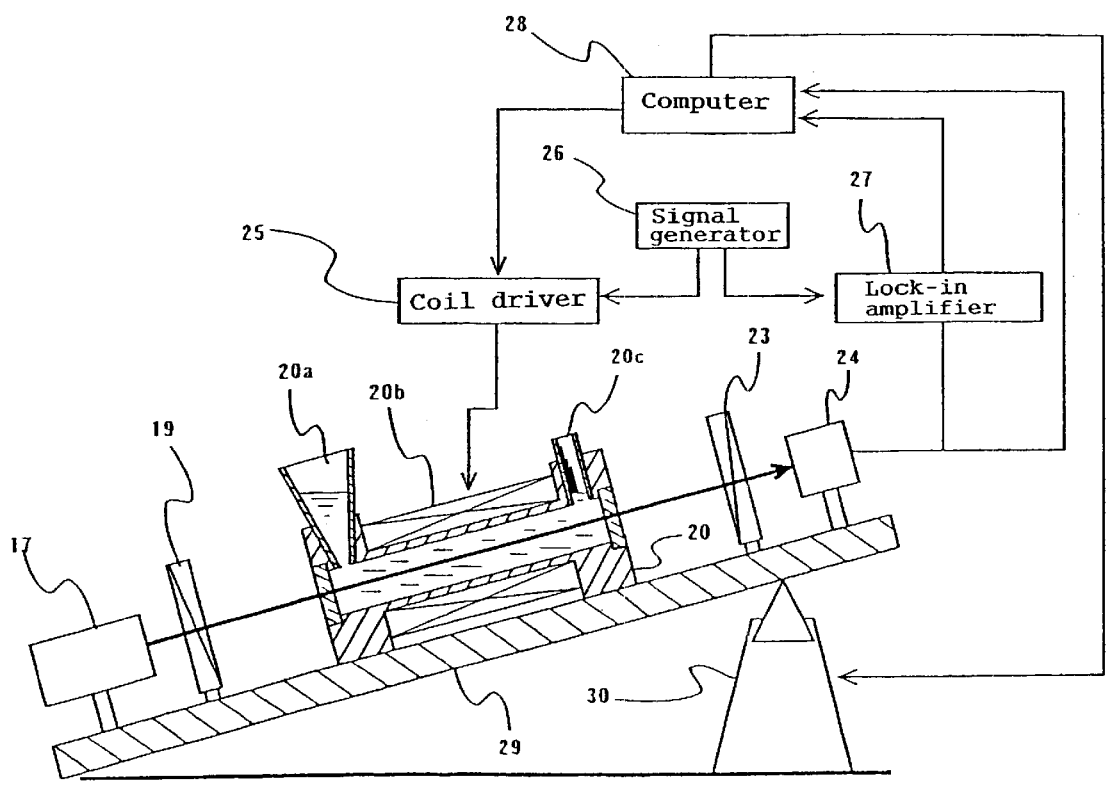
FIG. 4 is a schematic view illustrating a structure of a polarimeter used in a still further example in accordance with the present invention.

In this example, polarimetry will be described. FIG. 4 shows a schematic view of the polarimeter applied to the present invention. The polarimeter compensates a spontaneous optical rotation due to the sample by the so-called Faraday effect by applying a magnetic field thereto, and computes an angle of rotation based on a compensated value. Namely, the angle of rotation is derived based on the intensity of the magnetic field at the time when the angle of rotation due to spontaneous rotary power coincides to the angle of rotation due to Faraday effect.

The polarimeter in this example uses an identical light source for detection of interfering substances such as bubbles and for measurement of rotation angle.

A semiconductor laser module 17 projects almost parallel light having a wavelength of 670 mm, an intensity of 3.0 mW and a beam diameter of 2.0 mm. A polarizer 19 transmits only the light having a specific polarizing component from among a light projected from the semiconductor laser module 17. The light having passed through the polarizer 19 passes through a hollow space inside a sample cell 20 which accommodates a liquid sample. The sample cell 20 is fixed onto an inclined rail 29. The hollow space of the sample cell 20 is shaped in a cylinder and has an axial direction in correspondence with a direction of course of the projected light from the semiconductor laser module 17 as shown by an arrow in the figure. The projected light has a substantial optical path length of 50 mm.

An analyzer 23 is arranged on a posterior step of the sample cell 20. The analyzer 23 transmits only the component having a direction of polarization perpendicular to that of the light transmitted through the polarizer 19. An optical sensor 24 detects the light transmitted through the analyzer 23.

At a lower end of the hollow space of the inclined sample cell 20, a sample introducing port 20a is formed for introducing the sample into the hollow space. At an upper end of the hollow space, a ventilation port 20c is also formed.

Around the sample cell 20, a solenoid coil 20b is provided in order to apply a magnetic field to the sample in the hollow space in a direction of course of light. A coil driver 25 supplies a current to the solenoid coil 20b based on a command signal from a computer 28. At that time, a control signal to the solenoid coil 20b issued from the coil driver 25 is combined with a modulation signal, for example, a signal having an amplitude of 0.001 A and a frequency of 1.3 KHz issued from a signal generator 26.

A lock-in amplifier 27 makes a phase-sensitive detection for an output signal from the optical sensor 24 with reference to the modulation signal of the solenoid coil 20b.

The computer 28 supplies a control current signal to the coil driver 25 to make an output signal of the lock-in amplifier 0 at measurement of angle of rotation of the sample.

An optical system composed of the semiconductor laser module 17, polarizer 19, sample cell 20, analyzer 23 and optical sensor 24 is fixed to the rail 29. A lift 30 changes tilt of the sample cell 20 fixed onto the rail 29 by moving one end of the rail 29 up and down. The lift 30 is controlled by a command signal from the computer 28 based on an output signal from the optical sensor 24. More specifically, when any interfering substances such as bubbles and undissolved solute particles are present on the optical path in the sample cell 20, the computer 28 detects their presence based on a decrease in output from the optical sensor 24 and controls the lift 30 to shift the end of the rail 29 up and down. As a result, the interfering substances on the optical path in the sample cell 20 are moved and cleared from the optical path. This also promotes dissolution of the not yet dissolved solute particles. No detection of undissolved particles and bubbles generating during dissolution of those particles confirms complete dissolution of the solute to make a uniform concentration of the sample. The sample in this condition is measured for its optical properties.

As discussed above, the use of identical light source for detection of interfering substances and optical measurement particularly during measurement enables real time detection of any interfering substances with the measurement. This reduces the duration of discontinued measurement due to detection of interfering substances to a minimum. As a result, it is possible to make measurement of higher reliability in a shorter time. Similarly, when measurement starts after removal and disappearance of the interfering substances, the waiting time can be shortened to a minimum.

When urine is examined by measuring an angle of rotation, even if the urine is directly passed into the sample introducing port 20a of the sample cell 20, the interfering substances such as bubbles generating during urination can be removed safely, enabling high accuracy measurement of rotation angle.

This drastically improves handling and reliability of the device for measuring optical properties of a sample containing many bubbles, particularly urine immediately after urination. It is also possible to realize a compact and low cost device, which in turn promotes common use of the device.

According to the present invention, it is possible to eliminate the need of detaching the sample cell from an optical system to introduce or excrete the sample and facilitate precise measurement of optical properties of a liquid sample even when any interfering substances such as bubbles are present in the sample cell.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A method for controlling an optical property measurement system wherein optical properties of a liquid sample accommodated in a sample cell are measured by projecting a first light to the liquid sample to analyze light transmitted through the liquid sample, the method comprising the steps of:

projecting a second light to a path or a periphery of the path of the first light to detect a presence or absence of at least one of bubbles and particles in the sample which may interfere with transmission of the first light projected to the sample, based on an intensity of the second light, and removing the at least one of bubbles and particles in the sample from the path of the first light projected to the sample upon detection of the presence of at least one of bubbles and particles, wherein the intensity of the second light is greater than an intensity of the first light.

2. The method of controlling an optical property measurement system according to claim 1, wherein the at least one of bubbles and particles in the sample is removed from the path of the first light by vibrating the sample cell.

3. The method for controlling an optical property measurement system according to claim 1, wherein the at least one of bubbles and particles in the sample is removed from the path of the first light by stirring the sample cell.

4. The method for controlling an optical property measurement system according to claim 1, wherein the at least one of bubbles and particles in the sample is removed from the path of the first light by sliding a member along an inner wall of an entrance plane and an exit plane of the first light in the sample cell to remove the at least one of bubbles and particles attached to the inner wall.

5. The method for controlling an optical property measurement system according to claim 1, wherein the at least one of bubbles and particles in the sample is removed from the path of the first light by inclining the sample cell.

6. The method for controlling an optical property measurement system according to claim 1, wherein the sample is formulated inside the sample cell and further comprises the steps of:

destroying at least one of bubbles and particles of a solute which remain unsolved during formulation of the sample and which are detected in the projecting step, and confirming disappearance of the at least one of bubbles and particles of the solute prior to measuring the optical property of the sample.

7. A method for controlling an optical property measurement system wherein optical properties of a liquid sample accommodated in a sample cell are measured by projecting a first light to the liquid sample to analyze light transmitted through the liquid sample, the method comprising the steps of:

projecting a second light to a path or a periphery of the path of the first light to detect a presence or absence of at least one of bubbles and particles in the sample which may interfere with transmission of the first light projected to the sample, based on an intensity of the second light, and removing the at least one of bubbles and particles in the sample from the path of the first light projected to the sample upon detection of the presence of at least one of bubbles and particles, wherein the first light and the second light overlap while being projected to the liquid sample, and wherein the second light has a greater diameter than a diameter of the first light such that the second light covers the first light.

8. The method of controlling an optical property measurement system according to claim 7, wherein the at least one of bubbles and particles in the sample is removed from the path of the first light by vibrating the sample cell.

9. The method for controlling an optical property measurement system according to claim 7, wherein the at least one of bubbles and particles in the sample is removed from the path of the first light by stirring the sample cell.

10. The method for controlling an optical property measurement system according to claim 7, wherein the at least one of bubbles and particles in the sample is removed from the path of the first light by sliding a member along an inner wall of an entrance plane and an exit plane of the first light in the sample cell to remove the at least one of bubbles and particles attached to the inner wall.

11. The method for controlling an optical property measurement system according to claim 7, wherein the at least one of bubbles and particles in the sample is removed from the path of the first light by inclining the sample cell.

12. The method for controlling an optical property measurement system according to claim 7, wherein the sample is formulated inside the sample cell and further comprises the steps of:

destroying at least one of bubbles and particles of a solute which remain unsolved during formulation of the sample and which are detected in the projecting step, and confirming disappearance of the at least one of bubbles and particles of the solute prior to measuring the optical property of the sample.

* * * * *